(12) United States Patent
Ho et al.

(10) Patent No.: US 7,879,047 B2
(45) Date of Patent: Feb. 1, 2011

(54) SURGICAL CONNECTION APPARATUS AND METHODS

(75) Inventors: Liem Ho, Mountain View, CA (US); Steve Golden, Menlo Park, CA (US); Laurent Schaller, Los Altos, CA (US)

(73) Assignee: Medtronic, Inc., Minneapolis, MN (US)

( * ) Notice: Subject to any disclaimer, the term of this patent is extended or adjusted under 35 U.S.C. 154(b) by 1015 days.

(21) Appl. No.: 10/732,084

(22) Filed: Dec. 10, 2003

(65) Prior Publication Data
US 2005/0131429 A1 Jun. 16, 2005

(51) Int. Cl.
*A61B 17/10* (2006.01)
*A61B 17/08* (2006.01)
(52) U.S. Cl. ................... 606/142; 606/219
(58) Field of Classification Search .......... 606/142, 606/144, 148, 151, 191, 219, 139, 184, 185, 606/1, 222, 223; 227/175.1, 67, 68, 66; 24/16 PB; 604/264; 600/30
See application file for complete search history.

(56) References Cited

U.S. PATENT DOCUMENTS

| | | | |
|---|---|---|---|
| 43,098 | A | 6/1864 | Cooper |
| 636,728 | A | 11/1899 | Kindel |
| 655,190 | A | 8/1900 | Bramson |
| 1,087,186 | A | 2/1914 | Scholfield |
| 1,167,014 | A | 1/1916 | O'Brien |
| 1,539,221 | A | 5/1925 | John |
| 1,583,271 | A | 5/1926 | Biro |
| 1,625,602 | A | 4/1927 | Gould et al. |
| 1,867,624 | A | 7/1932 | Hoffman |
| 2,201,610 | A | 5/1940 | Dawson |
| 2,240,330 | A | 4/1941 | Flagg et al. |
| 2,256,382 | A | 9/1941 | Dole |
| 2,264,679 | A | 12/1941 | Ravel |
| 2,413,142 | A | 12/1946 | Jones et al. |
| 2,430,293 | A | 11/1947 | Howells |

(Continued)

FOREIGN PATENT DOCUMENTS

DE 0219999 3/1910

(Continued)

OTHER PUBLICATIONS

US 5,002,663, 03/1991, Pyka et al. (withdrawn).

(Continued)

*Primary Examiner*—Julian W Woo
(74) *Attorney, Agent, or Firm*—Mike Jaro; Jeffrey J. Hohenshell

(57) ABSTRACT

Surgical connection apparatus comprises a support having a proximal portion with a distal end and a proximal portion. The support forms a pathway between the proximal and distal portions. A plurality of self-closing clips are slidably disposed in the pathway and a pusher is arranged to slidably move in the pathway and push the clips in a distal direction. The apparatus facilitates partial ejection of a clip after which the remainder of the clip is withdrawn therefrom. In one embodiment, the support comprises a tubular needle with the distal end being pointed. The needle can be used to penetrate the tissue or material to be joined and to manipulate or approximate tissue or material to be joined before the clip is partially ejected.

18 Claims, 3 Drawing Sheets

U.S. PATENT DOCUMENTS

| | | |
|---|---|---|
| 2,505,358 A | 4/1950 | Gusberg et al. |
| 2,516,710 A | 7/1950 | Mascolo |
| 2,715,486 A | 8/1955 | Marcoff-Moghadam |
| 2,890,519 A | 6/1959 | Storz, Jr. |
| 2,940,452 A | 6/1960 | Smialowski |
| 3,055,689 A | 9/1962 | Jorgensen |
| 3,057,355 A | 10/1962 | Smialowski |
| 3,082,426 A | 3/1963 | Miles |
| 3,143,742 A | 8/1964 | Cromie |
| 3,150,379 A | 9/1964 | Brown |
| 3,180,337 A | 4/1965 | Smialowski |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| 3,656,185 A | 4/1972 | Carpentier |
| RE27,391 E | 6/1972 | Merser |
| 3,753,438 A | 8/1973 | Wood et al. |
| 3,762,418 A | 10/1973 | Wasson |
| 3,776,237 A | 12/1973 | Hill et al. |
| 3,802,438 A | 4/1974 | Wolvek |
| 3,815,798 A * | 6/1974 | Lavitch et al. ............... 227/67 |
| 3,825,009 A | 7/1974 | Williams |
| 3,837,345 A | 9/1974 | Matar |
| 3,874,388 A | 4/1975 | King et al. |
| 3,875,648 A | 4/1975 | Bone |
| 3,905,403 A | 9/1975 | Smith et al. |
| 3,908,662 A | 9/1975 | Razgulov et al. |
| 3,910,281 A | 10/1975 | Kletschka et al. |
| 3,958,576 A | 5/1976 | Komiya |
| 3,976,079 A | 8/1976 | Samuels |
| 3,995,619 A | 12/1976 | Glatzer |
| 4,006,747 A | 2/1977 | Kronenthal et al. |
| 4,018,228 A | 4/1977 | Goosen |
| 4,038,725 A | 8/1977 | Keefe |
| 4,042,979 A | 8/1977 | Angell |
| 4,073,179 A | 2/1978 | Hickey et al. |
| 4,103,690 A | 8/1978 | Harris |
| 4,111,206 A | 9/1978 | Vishnevsky et al. |
| 4,129,059 A | 12/1978 | Van Eck |
| 4,140,125 A | 2/1979 | Smith |
| 4,170,990 A | 10/1979 | Baumgart et al. |
| 4,185,636 A | 1/1980 | Gabbay et al. |
| 4,192,315 A | 3/1980 | Hilzinger et al. |
| 4,201,314 A * | 5/1980 | Samuels et al. ............ 606/151 |
| 4,214,587 A | 7/1980 | Sakura |
| 4,217,902 A | 8/1980 | March |
| 4,243,048 A | 1/1981 | Griffin |
| 4,324,248 A | 4/1982 | Perlin |
| 4,345,601 A | 8/1982 | Fukuda |
| 4,352,358 A | 10/1982 | Angelchik |
| 4,366,819 A | 1/1983 | Kaster |
| 4,396,139 A | 8/1983 | Hall et al. |
| 4,416,266 A | 11/1983 | Baucom |
| 4,456,017 A | 6/1984 | Miles |
| 4,465,071 A | 8/1984 | Samuels et al. |
| 4,470,415 A | 9/1984 | Wozniak |
| 4,470,533 A | 9/1984 | Schuler |
| 4,474,181 A | 10/1984 | Schenck |
| 4,485,816 A | 12/1984 | Krumme |
| 4,492,229 A | 1/1985 | Grunwald |
| 4,522,207 A | 6/1985 | Kleiman et al. |
| 4,523,592 A | 6/1985 | Daniel |
| 4,532,927 A | 8/1985 | Miksza |
| 4,535,764 A | 8/1985 | Ebert |
| 4,549,545 A | 10/1985 | Levy |
| 4,553,542 A | 11/1985 | Schenck et al. |
| 4,576,605 A | 3/1986 | Kaidash et al. |
| 4,586,502 A | 5/1986 | Bedi et al. |
| 4,586,503 A | 5/1986 | Kirsch et al. |
| 4,593,693 A | 6/1986 | Schenck |
| 4,595,007 A | 6/1986 | Mericle |
| 4,612,932 A | 9/1986 | Caspar et al. |
| 4,622,970 A | 11/1986 | Wozniak |
| 4,624,255 A | 11/1986 | Schenck et al. |
| 4,637,380 A | 1/1987 | Orejola |
| 4,641,652 A * | 2/1987 | Hutterer et al. ............ 606/148 |
| 4,653,496 A | 3/1987 | Bundy et al. |
| 4,665,906 A | 5/1987 | Jervis |
| 4,665,917 A | 5/1987 | Clanton et al. |
| 4,683,895 A | 8/1987 | Pohndorf |
| 4,706,362 A * | 11/1987 | Strausburg ................... 227/67 |
| 4,719,917 A | 1/1988 | Barrows et al. |
| 4,719,924 A | 1/1988 | Crittenden et al. |
| 4,730,615 A | 3/1988 | Sutherland et al. |
| 4,732,151 A | 3/1988 | Jones |
| 4,809,695 A | 3/1989 | Gwathmey et al. |
| 4,820,298 A | 4/1989 | Leveen et al. |
| 4,844,318 A * | 7/1989 | Kunreuther .................. 227/67 |
| 4,873,975 A | 10/1989 | Walsh et al. |
| 4,890,615 A | 1/1990 | Caspari et al. |
| 4,896,668 A | 1/1990 | Popoff et al. |
| 4,899,744 A | 2/1990 | Fujitsuka et al. |
| 4,901,721 A | 2/1990 | Hakki |
| 4,923,461 A | 5/1990 | Caspari et al. |
| 4,924,866 A | 5/1990 | Yoon |
| 4,926,860 A | 5/1990 | Stice et al. |
| 4,929,240 A | 5/1990 | Kirsch et al. |
| 4,930,674 A | 6/1990 | Barak |
| 4,932,955 A | 6/1990 | Merz et al. |
| 4,935,027 A | 6/1990 | Yoon |
| 4,950,015 A | 8/1990 | Nejib et al. |
| 4,950,283 A | 8/1990 | Dzubow et al. |
| 4,950,285 A | 8/1990 | Wilk |
| 4,957,498 A | 9/1990 | Caspari et al. |
| 4,983,176 A | 1/1991 | Cushman et al. |
| 4,990,152 A | 2/1991 | Yoon |
| 4,991,567 A | 2/1991 | McCuen et al. |
| 4,994,069 A | 2/1991 | Ritchart et al. |
| 4,997,439 A | 3/1991 | Chen |
| 5,002,550 A | 3/1991 | Li |
| 5,002,562 A | 3/1991 | Oberlander |
| 5,007,920 A | 4/1991 | Torre |
| 5,011,481 A | 4/1991 | Myers et al. |
| 5,020,713 A * | 6/1991 | Kunreuther .................. 227/67 |
| 5,026,379 A | 6/1991 | Yoon |
| 5,032,127 A | 7/1991 | Frazee et al. |
| 5,035,692 A | 7/1991 | Lyon et al. |
| 5,035,702 A | 7/1991 | Taheri |
| 5,042,707 A | 8/1991 | Taheri |
| 5,047,047 A | 9/1991 | Yoon |
| 5,053,047 A | 10/1991 | Yoon |
| 5,064,431 A | 11/1991 | Gilbertson et al. |
| 5,074,874 A | 12/1991 | Yoon et al. |
| 5,088,692 A | 2/1992 | Weiler |
| 5,100,418 A | 3/1992 | Yoon |
| 5,100,421 A | 3/1992 | Christoudias |
| 5,104,407 A | 4/1992 | Lam et al. |
| 5,119,983 A | 6/1992 | Green et al. |
| 5,123,913 A | 6/1992 | Wilk et al. |
| 5,127,413 A | 7/1992 | Ebert |
| 5,129,913 A | 7/1992 | Ruppert |
| 5,152,769 A | 10/1992 | Baber |
| 5,154,189 A | 10/1992 | Oberlander |
| 5,158,566 A | 10/1992 | Pianetti |
| 5,171,250 A | 12/1992 | Yoon |
| 5,171,252 A | 12/1992 | Friedland |
| 5,174,087 A | 12/1992 | Bruno |
| 5,178,634 A | 1/1993 | Ramos Martinez |

| | | | | | | |
|---|---|---|---|---|---|---|
| 5,192,294 A | 3/1993 | Blake | | 5,500,000 A | 3/1996 | Feagin et al. |
| 5,196,022 A | 3/1993 | Bilweis | | 5,522,884 A | 6/1996 | Wright |
| 5,201,880 A | 4/1993 | Wright et al. | | 5,527,342 A | 6/1996 | Pietrzak et al. |
| 5,207,694 A | 5/1993 | Broome | | 5,533,236 A | 7/1996 | Tseng |
| 5,217,027 A | 6/1993 | Hermens | | 5,538,509 A | 7/1996 | Dunlap et al. |
| 5,219,358 A | 6/1993 | Bendel et al. | | 5,545,214 A | 8/1996 | Stevens |
| 5,221,259 A | 6/1993 | Weldon et al. | | 5,549,619 A | 8/1996 | Peters et al. |
| 5,222,961 A | 6/1993 | Nakao et al. | | 5,556,411 A * | 9/1996 | Taoda et al. .................. 606/185 |
| 5,222,976 A | 6/1993 | Yoon | | 5,562,685 A * | 10/1996 | Mollenauer et al. ......... 606/148 |
| 5,234,447 A | 8/1993 | Kaster et al. | | 5,569,205 A | 10/1996 | Hart et al. |
| 5,236,440 A | 8/1993 | Hlavacek | | 5,569,274 A | 10/1996 | Rapacki et al. |
| 5,242,456 A | 9/1993 | Nash et al. | | 5,569,301 A | 10/1996 | Granger et al. |
| 5,242,457 A | 9/1993 | Akopov et al. | | 5,571,119 A | 11/1996 | Atala |
| 5,246,443 A | 9/1993 | Mai | | 5,571,175 A | 11/1996 | Vanney et al. |
| 5,250,053 A | 10/1993 | Snyder | | 5,582,616 A | 12/1996 | Bolduc et al. |
| 5,258,011 A | 11/1993 | Drews | | 5,582,619 A * | 12/1996 | Ken .......................... 606/191 |
| 5,261,917 A | 11/1993 | Hasson et al. | | 5,584,879 A | 12/1996 | Reimold et al. |
| 5,269,783 A | 12/1993 | Sander | | 5,586,983 A | 12/1996 | Sanders et al. |
| 5,269,809 A | 12/1993 | Hayhurst et al. | | 5,591,179 A | 1/1997 | Edelstein |
| 5,282,825 A | 2/1994 | Muck et al. | | 5,593,414 A | 1/1997 | Shipp et al. |
| 5,290,289 A | 3/1994 | Sanders et al. | | 5,593,424 A | 1/1997 | Northrupp, III |
| 5,304,117 A | 4/1994 | Wilk | | 5,597,378 A | 1/1997 | Jervis |
| 5,304,204 A | 4/1994 | Bregen | | 5,601,571 A * | 2/1997 | Moss ......................... 606/144 |
| 5,306,296 A | 4/1994 | Wright et al. | | 5,601,572 A | 2/1997 | Middleman et al. |
| 5,312,436 A | 5/1994 | Coffey et al. | | 5,601,600 A | 2/1997 | Ton |
| 5,314,468 A | 5/1994 | Ramos Martinez | | 5,603,718 A | 2/1997 | Xu |
| 5,330,503 A | 7/1994 | Yoon | | 5,609,608 A | 3/1997 | Bennett et al. |
| 5,334,196 A | 8/1994 | Scott et al. | | 5,618,311 A | 4/1997 | Gryskiewicz et al. |
| 5,336,233 A | 8/1994 | Chen | | 5,628,757 A | 5/1997 | Hasson |
| 5,336,239 A | 8/1994 | Gimpelson | | 5,630,540 A | 5/1997 | Blewett |
| 5,346,459 A | 9/1994 | Allen | | 5,632,752 A | 5/1997 | Buelna |
| 5,350,420 A | 9/1994 | Cosgrove et al. | | 5,632,753 A | 5/1997 | Loeser |
| 5,353,804 A | 10/1994 | Kornberg et al. | | 5,643,295 A | 7/1997 | Yoon |
| 5,355,897 A | 10/1994 | Pietrafitta et al. | | 5,643,305 A | 7/1997 | Al-Tameem |
| 5,356,424 A | 10/1994 | Buzerak et al. | | 5,645,568 A | 7/1997 | Chervitz et al. |
| 5,364,406 A | 11/1994 | Sewell | | 5,653,716 A | 8/1997 | Malo et al. |
| 5,366,459 A | 11/1994 | Yoon | | 5,653,718 A | 8/1997 | Yoon |
| 5,366,462 A | 11/1994 | Kaster et al. | | 5,658,312 A | 8/1997 | Green et al. |
| 5,366,479 A | 11/1994 | McGarry et al. | | 5,660,186 A | 8/1997 | Bachir |
| 5,374,268 A | 12/1994 | Sander | | 5,665,109 A | 9/1997 | Yoon |
| 5,376,096 A | 12/1994 | Foster | | 5,669,918 A | 9/1997 | Balazs et al. |
| 5,382,259 A | 1/1995 | Phelps et al. | | 5,676,670 A | 10/1997 | Kim |
| 5,383,904 A | 1/1995 | Totakura et al. | | 5,683,417 A | 11/1997 | Cooper |
| 5,387,227 A | 2/1995 | Grice | | 5,690,662 A | 11/1997 | Chiu et al. |
| 5,403,331 A | 4/1995 | Chesterfield | | 5,695,504 A | 12/1997 | Gifford, III et al. |
| 5,403,333 A | 4/1995 | Kaster et al. | | 5,695,505 A | 12/1997 | Yoon |
| 5,403,338 A | 4/1995 | Milo | | 5,697,913 A | 12/1997 | Sierocuk et al. |
| 5,403,346 A | 4/1995 | Loeser | | 5,697,943 A | 12/1997 | Sauer et al. |
| 5,413,584 A | 5/1995 | Schulze | | 5,700,270 A | 12/1997 | Peyser et al. |
| 5,417,684 A | 5/1995 | Jackson et al. | | 5,700,271 A | 12/1997 | Whitfield et al. |
| 5,417,700 A | 5/1995 | Egan | | 5,702,412 A | 12/1997 | Popov et al. |
| 5,423,821 A | 6/1995 | Pasque | | 5,707,362 A | 1/1998 | Yoon |
| 5,431,666 A | 7/1995 | Sauer et al. | | 5,707,380 A | 1/1998 | Hinchliffe et al. |
| 5,437,680 A | 8/1995 | Yoon | | 5,709,693 A | 1/1998 | Taylor |
| 5,437,681 A | 8/1995 | Meade et al. | | 5,709,695 A | 1/1998 | Northrup, III |
| 5,437,685 A | 8/1995 | Blasnik | | 5,715,987 A | 2/1998 | Kelley et al. |
| 5,439,479 A | 8/1995 | Schichman et al. | | 5,716,370 A | 2/1998 | Williamson, IV et al. |
| 5,445,167 A | 8/1995 | Yoon et al. | | 5,720,755 A | 2/1998 | Dakov |
| 5,445,644 A | 8/1995 | Pietrafitta et al. | | 5,725,539 A | 3/1998 | Matern |
| 5,450,860 A | 9/1995 | O'Connor | | 5,725,542 A | 3/1998 | Yoon |
| 5,451,231 A | 9/1995 | Rabenau et al. | | 5,725,554 A | 3/1998 | Simon et al. |
| 5,452,733 A | 9/1995 | Sterman et al. | | 5,728,135 A | 3/1998 | Bregen et al. |
| 5,454,834 A | 10/1995 | Boebel et al. | | 5,732,872 A | 3/1998 | Bolduc et al. |
| 5,456,246 A | 10/1995 | Schmiedling et al. | | 5,735,290 A | 4/1998 | Sterman et al. |
| 5,462,561 A | 10/1995 | Voda | | 5,746,753 A | 5/1998 | Sullivan et al. |
| 5,474,557 A | 12/1995 | Mai | | 5,755,778 A | 5/1998 | Kleshinski |
| 5,480,405 A | 1/1996 | Yoon | | 5,766,189 A | 6/1998 | Matsumo |
| 5,486,187 A | 1/1996 | Schenck | | 5,769,870 A | 6/1998 | Salahich et al. |
| 5,486,197 A | 1/1996 | Le et al. | | 5,779,718 A | 7/1998 | Green et al. |
| 5,488,958 A | 2/1996 | Topel et al. | | 5,782,397 A | 7/1998 | Koukline |
| 5,489,057 A * | 2/1996 | Deschenes .................. 227/67 | | 5,782,844 A * | 7/1998 | Yoon et al. .................. 606/142 |
| 5,496,334 A | 3/1996 | Klundt et al. | | 5,797,920 A | 8/1998 | Kim |
| 5,499,990 A | 3/1996 | Schulken et al. | | 5,797,933 A | 8/1998 | Snow et al. |

| | | | | | | |
|---|---|---|---|---|---|---|
| 5,797,934 A | 8/1998 | Rygaard | | 6,013,084 A | 1/2000 | Ken et al. |
| 5,797,960 A | 8/1998 | Stevens et al. | | 6,022,367 A | 2/2000 | Sherts |
| 5,799,661 A | 9/1998 | Boyd et al. | | 6,024,748 A | 2/2000 | Manzo et al. |
| 5,799,857 A | 9/1998 | Robertson et al. | | 6,032,849 A | 3/2000 | Mastri et al. |
| 5,810,848 A * | 9/1998 | Hayhurst ............... 606/144 | | 6,033,419 A | 3/2000 | Hamblin, Jr. et al. |
| 5,810,851 A * | 9/1998 | Yoon ..................... 606/148 | | 6,036,699 A | 3/2000 | Andreas et al. |
| 5,810,853 A | 9/1998 | Yoon | | 6,036,703 A | 3/2000 | Evans et al. |
| 5,810,882 A | 9/1998 | Bolduc et al. | | 6,036,710 A | 3/2000 | McGarry et al. |
| 5,817,113 A | 10/1998 | Gifford, III et al. | | 6,042,607 A | 3/2000 | Williamson et al. |
| 5,820,631 A | 10/1998 | Nobles | | 6,056,751 A | 5/2000 | Fenton |
| 5,824,002 A | 10/1998 | Gentelia et al. | | 6,063,070 A | 5/2000 | Eder |
| 5,824,008 A | 10/1998 | Bolduc et al. | | 6,066,148 A | 5/2000 | Rygaard |
| 5,827,265 A | 10/1998 | Glinsky et al. | | 6,074,401 A | 6/2000 | Gardiner et al. |
| 5,827,316 A | 10/1998 | Young et al. | | 6,074,418 A | 6/2000 | Buchanan et al. |
| 5,830,221 A | 11/1998 | Stein et al. | | 6,077,291 A | 6/2000 | Das |
| 5,830,222 A | 11/1998 | Makower | | 6,080,114 A | 6/2000 | Russin |
| 5,833,698 A | 11/1998 | Hinchliffe | | 6,083,237 A | 7/2000 | Huitema et al. |
| 5,849,019 A | 12/1998 | Yoon | | 6,106,538 A | 8/2000 | Shiber |
| 5,851,216 A | 12/1998 | Allen | | 6,110,188 A | 8/2000 | Narciso |
| 5,855,614 A | 1/1999 | Stevens et al. | | 6,113,611 A | 9/2000 | Allen et al. |
| 5,868,702 A | 2/1999 | Stevens et al. | | 6,113,612 A | 9/2000 | Swanson et al. |
| 5,868,763 A | 2/1999 | Spence et al. | | 6,120,524 A | 9/2000 | Taheri |
| 5,871,528 A | 2/1999 | Camps et al. | | 6,132,438 A | 10/2000 | Fleischmann et al. |
| 5,879,371 A | 3/1999 | Gardiner et al. | | 6,139,540 A | 10/2000 | Rost et al. |
| 5,881,943 A | 3/1999 | Heck et al. | | 6,143,004 A | 11/2000 | Davis et al. |
| 5,882,340 A | 3/1999 | Yoon | | 6,149,658 A | 11/2000 | Gardiner et al. |
| 5,891,130 A | 4/1999 | Palermo et al. | | 6,152,935 A * | 11/2000 | Kammerer et al. .......... 606/144 |
| 5,891,160 A | 4/1999 | Williamson, IV et al. | | 6,152,937 A | 11/2000 | Peterson et al. |
| 5,893,369 A | 4/1999 | LeMole | | 6,159,165 A | 12/2000 | Ferrera et al. |
| 5,893,856 A | 4/1999 | Jacob et al. | | 6,159,225 A | 12/2000 | Makower |
| 5,893,865 A | 4/1999 | Swindle et al. | | 6,162,233 A | 12/2000 | Williamson, IV et al. |
| 5,893,886 A | 4/1999 | Zegdi et al. | | 6,165,183 A | 12/2000 | Kuehn et al. |
| 5,895,394 A | 4/1999 | Kienzle et al. | | 6,165,185 A | 12/2000 | Shennib et al. |
| 5,904,697 A | 5/1999 | Gifford, III et al. | | 6,171,320 B1 | 1/2001 | Monassevitch |
| 5,908,428 A | 6/1999 | Scirica et al. | | 6,171,321 B1 | 1/2001 | Gifford, III et al. |
| 5,911,352 A | 6/1999 | Racenet et al. | | 6,176,413 B1 | 1/2001 | Heck et al. |
| 5,919,207 A | 7/1999 | Taheri | | 6,176,864 B1 | 1/2001 | Chapman |
| 5,931,842 A | 8/1999 | Goldsteen et al. | | 6,179,840 B1 | 1/2001 | Bowman |
| 5,941,434 A | 8/1999 | Green | | 6,179,848 B1 | 1/2001 | Solem |
| 5,941,439 A * | 8/1999 | Kammerer et al. ............ 227/67 | | 6,179,849 B1 | 1/2001 | Yencho et al. |
| 5,941,442 A | 8/1999 | Geiste et al. | | 6,183,512 B1 | 2/2001 | Howanec et al. |
| 5,941,888 A | 8/1999 | Wallace et al. | | 6,190,373 B1 | 2/2001 | Palermo et al. |
| 5,941,908 A | 8/1999 | Goldsteen et al. | | 6,193,733 B1 | 2/2001 | Adams |
| 5,944,730 A | 8/1999 | Nobles et al. | | 6,193,734 B1 | 2/2001 | Bolduc et al. |
| 5,951,576 A | 9/1999 | Wakabayashi | | 6,197,037 B1 | 3/2001 | Hair |
| 5,951,600 A | 9/1999 | Lemelson | | 6,217,611 B1 | 4/2001 | Klostermeyer |
| 5,954,735 A | 9/1999 | Rygaard | | 6,221,083 B1 | 4/2001 | Mayer |
| 5,957,363 A | 9/1999 | Heck | | 6,241,738 B1 | 6/2001 | Dereume |
| 5,957,938 A | 9/1999 | Zhu et al. | | 6,241,741 B1 | 6/2001 | Duhaylongsod et al. |
| 5,957,940 A | 9/1999 | Tanner et al. | | 6,248,117 B1 | 6/2001 | Blatter |
| 5,961,481 A | 10/1999 | Sterman et al. | | 6,250,308 B1 | 6/2001 | Cox |
| 5,961,539 A | 10/1999 | Northrup, III et al. | | 6,254,615 B1 | 7/2001 | Bolduc et al. |
| 5,964,772 A | 10/1999 | Bolduc et al. | | 6,269,819 B1 | 8/2001 | Oz et al. |
| 5,964,782 A | 10/1999 | Lafontaine et al. | | 6,280,460 B1 | 8/2001 | Bolduc et al. |
| 5,972,001 A * | 10/1999 | Yoon ..................... 606/139 | | 6,283,979 B1 | 9/2001 | Mers Kelly et al. |
| 5,972,004 A | 10/1999 | Williamson, IV et al. | | 6,283,993 B1 | 9/2001 | Cosgrove et al. |
| 5,972,024 A | 10/1999 | Northrup, III et al. | | 6,296,622 B1 | 10/2001 | Kurz et al. |
| 5,976,159 A | 11/1999 | Bolduc et al. | | 6,296,656 B1 | 10/2001 | Bolduc et al. |
| 5,976,161 A | 11/1999 | Kirsch et al. | | 6,306,141 B1 | 10/2001 | Jervis |
| 5,976,164 A | 11/1999 | Bencini et al. | | 6,332,893 B1 | 12/2001 | Mortier et al. |
| 5,976,178 A | 11/1999 | Goldsteen et al. | | 6,346,074 B1 | 2/2002 | Roth |
| 5,984,917 A | 11/1999 | Fleischmann et al. | | 6,346,112 B2 | 2/2002 | Adams |
| 5,984,959 A | 11/1999 | Robertson et al. | | 6,350,269 B1 | 2/2002 | Shipp et al. |
| 5,989,242 A | 11/1999 | Saadat et al. | | 6,352,543 B1 | 3/2002 | Cole |
| 5,989,268 A | 11/1999 | Pugsley, Jr. et al. | | 6,358,258 B1 | 3/2002 | Arcia et al. |
| 5,989,276 A | 11/1999 | Houser et al. | | 6,361,559 B1 | 3/2002 | Houser et al. |
| 5,989,278 A | 11/1999 | Mueller | | 6,368,348 B1 | 4/2002 | Gabbay |
| 5,993,465 A | 11/1999 | Shipp et al. | | 6,371,964 B1 | 4/2002 | Vargas et al. |
| 5,993,468 A | 11/1999 | Rygaard | | 6,387,105 B1 | 5/2002 | Gifford, III et al. |
| 5,997,556 A | 12/1999 | Tanner | | 6,391,038 B2 | 5/2002 | Vargas et al. |
| 6,001,110 A | 12/1999 | Adams | | 6,402,764 B1 | 6/2002 | Hendricksen et al. |
| 6,007,544 A | 12/1999 | Kim | | 6,406,492 B1 | 6/2002 | Lytle |
| 6,010,531 A | 1/2000 | Donlon et al. | | 6,406,493 B1 | 6/2002 | Tu et al. |

| Patent/Publication | Date | Inventors |
|---|---|---|
| 6,409,739 B1 | 6/2002 | Nobles et al. |
| 6,409,758 B2 | 6/2002 | Stobie et al. |
| 6,416,527 B1 | 7/2002 | Berg et al. |
| 6,418,597 B1 * | 7/2002 | Deschenes et al. ........ 24/16 PB |
| 6,419,658 B1 | 7/2002 | Restelli et al. |
| 6,419,681 B1 | 7/2002 | Vargas et al. |
| 6,419,695 B1 | 7/2002 | Gabbay |
| 6,425,900 B1 | 7/2002 | Knodel et al. |
| 6,428,550 B1 | 8/2002 | Vargas et al. |
| 6,428,555 B1 | 8/2002 | Koster, Jr. |
| 6,451,048 B1 | 9/2002 | Berg et al. |
| 6,461,320 B1 | 10/2002 | Yencho et al. |
| 6,475,222 B1 | 11/2002 | Berg et al. |
| 6,478,804 B2 | 11/2002 | Vargas et al. |
| 6,485,496 B1 | 11/2002 | Suyker et al. |
| 6,491,707 B2 | 12/2002 | Makower et al. |
| 6,497,671 B2 | 12/2002 | Ferrera et al. |
| 6,497,710 B2 | 12/2002 | Yencho et al. |
| 6,514,265 B2 | 2/2003 | Ho et al. |
| 6,517,558 B2 | 2/2003 | Gittings et al. |
| 6,524,338 B1 | 2/2003 | Gundry |
| 6,533,812 B2 | 3/2003 | Swanson et al. |
| 6,537,248 B2 | 3/2003 | Mulier et al. |
| 6,537,288 B2 | 3/2003 | Vargas et al. |
| 6,547,799 B2 | 4/2003 | Hess et al. |
| 6,551,332 B1 | 4/2003 | Nguyen et al. |
| 6,562,053 B2 | 5/2003 | Schulze et al. |
| 6,575,985 B2 | 6/2003 | Knight et al. |
| 6,589,255 B2 | 7/2003 | Schulze et al. |
| 6,607,541 B1 | 8/2003 | Gardiner et al. |
| 6,607,542 B1 | 8/2003 | Wild et al. |
| 6,613,059 B2 | 9/2003 | Schaller et al. |
| 6,629,988 B2 | 10/2003 | Weadock |
| 6,635,214 B2 | 10/2003 | Rapacki et al. |
| 6,641,593 B1 | 11/2003 | Schaller et al. |
| 6,648,900 B2 | 11/2003 | Fleischman et al. |
| 6,651,670 B2 | 11/2003 | Rapacki et al. |
| 6,651,672 B2 | 11/2003 | Roth |
| 6,652,540 B1 | 11/2003 | Cole et al. |
| 6,652,541 B1 | 11/2003 | Vargas et al. |
| 6,660,015 B1 | 12/2003 | Berg et al. |
| 6,682,540 B1 | 1/2004 | Sancoff et al. |
| 6,695,859 B1 | 2/2004 | Golden et al. |
| 6,702,826 B2 | 3/2004 | Liddicoat et al. |
| 6,709,442 B2 | 3/2004 | Miller et al. |
| 6,712,829 B2 | 3/2004 | Schulze |
| 6,719,768 B1 | 4/2004 | Cole et al. |
| 6,743,243 B1 | 6/2004 | Roy et al. |
| 6,749,622 B2 | 6/2004 | McGuckin et al. |
| 6,776,782 B2 | 8/2004 | Schulze |
| 6,776,784 B2 * | 8/2004 | Ginn ........................ 606/151 |
| 6,776,785 B2 | 8/2004 | Yencho et al. |
| 6,802,847 B1 | 10/2004 | Carson et al. |
| 6,821,286 B1 | 11/2004 | Carranza et al. |
| 6,869,444 B2 | 3/2005 | Gabbay |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,945,980 B2 | 9/2005 | Nguyen et al. |
| 6,955,679 B1 | 10/2005 | Hendricksen et al. |
| 6,960,221 B2 | 11/2005 | Ho et al. |
| 6,979,337 B2 | 12/2005 | Kato |
| 6,979,338 B1 | 12/2005 | Loshakove et al. |
| 7,022,131 B1 | 4/2006 | Derowe et al. |
| 7,056,330 B2 * | 6/2006 | Gayton ..................... 606/219 |
| 7,063,711 B1 | 6/2006 | Loshakove et al. |
| 7,070,618 B2 | 7/2006 | Streeter |
| 7,104,949 B2 | 9/2006 | Anderson et al. |
| 7,182,769 B2 | 2/2007 | Ainsworth et al. |
| 7,220,265 B2 | 5/2007 | Chanduszko et al. |
| 7,220,268 B2 | 5/2007 | Blatter |
| 7,267,645 B2 * | 9/2007 | Anderson et al. ............. 600/30 |
| RE40,377 E | 6/2008 | Williamson, IV et al. |
| 7,547,313 B2 | 6/2009 | Gardiner et al. |
| 7,722,643 B2 | 5/2010 | Schaller et al. |
| 7,744,611 B2 | 6/2010 | Nguyen et al. |
| 7,763,040 B2 | 7/2010 | Schaller et al. |
| 2001/0018592 A1 | 8/2001 | Schaller et al. |
| 2001/0018593 A1 | 8/2001 | Nguyen et al. |
| 2001/0018611 A1 | 8/2001 | Solem et al. |
| 2001/0021856 A1 | 9/2001 | Bolduc et al. |
| 2001/0047181 A1 | 11/2001 | Ho et al. |
| 2002/0010490 A1 | 1/2002 | Schaller et al. |
| 2002/0042623 A1 | 4/2002 | Blatter et al. |
| 2002/0082614 A1 | 6/2002 | Logan et al. |
| 2002/0099395 A1 | 7/2002 | Acampora et al. |
| 2002/0151916 A1 | 10/2002 | Muramatsu et al. |
| 2002/0165561 A1 | 11/2002 | Ainsworth et al. |
| 2002/0173803 A1 | 11/2002 | Yang et al. |
| 2003/0074012 A1 | 4/2003 | Nguyen et al. |
| 2003/0078603 A1 | 4/2003 | Schaller et al. |
| 2003/0083742 A1 | 5/2003 | Spence et al. |
| 2003/0093118 A1 | 5/2003 | Ho et al. |
| 2003/0125755 A1 | 7/2003 | Schaller et al. |
| 2003/0191481 A1 | 10/2003 | Nguyen et al. |
| 2003/0195531 A1 | 10/2003 | Nguyen et al. |
| 2003/0199974 A1 | 10/2003 | Lee et al. |
| 2004/0044406 A1 | 3/2004 | Woolfson et al. |
| 2004/0050393 A1 | 3/2004 | Golden et al. |
| 2004/0068276 A1 | 4/2004 | Golden et al. |
| 2004/0093024 A1 | 5/2004 | Lousararian et al. |
| 2004/0102797 A1 | 5/2004 | Golden et al. |
| 2004/0111099 A1 | 6/2004 | Nguyen et al. |
| 2004/0122514 A1 | 6/2004 | Fogarty et al. |
| 2004/0138685 A1 | 7/2004 | Clague et al. |
| 2004/0167573 A1 | 8/2004 | Williamson et al. |
| 2004/0176663 A1 | 9/2004 | Edoga |
| 2004/0193259 A1 | 9/2004 | Gabbay |
| 2005/0004582 A1 | 1/2005 | Edoga |
| 2005/0021054 A1 | 1/2005 | Ainsworth et al. |
| 2005/0043749 A1 | 2/2005 | Breton et al. |
| 2005/0065601 A1 | 3/2005 | Lee et al. |
| 2005/0070924 A1 | 3/2005 | Schaller et al. |
| 2005/0075659 A1 | 4/2005 | Realyvasquez et al. |
| 2005/0075667 A1 | 4/2005 | Schaller et al. |
| 2005/0080454 A1 | 4/2005 | Drews |
| 2005/0101975 A1 | 5/2005 | Nguyen et al. |
| 2005/0107871 A1 | 5/2005 | Realyvasquez et al. |
| 2005/0131429 A1 | 6/2005 | Ho et al. |
| 2005/0267572 A1 | 12/2005 | Schoon et al. |
| 2006/0004389 A1 | 1/2006 | Nguyen et al. |
| 2006/0122634 A1 | 6/2006 | Ino et al. |
| 2006/0253143 A1 | 11/2006 | Edoga |
| 2006/0271081 A1 | 11/2006 | Realyvasquez |
| 2006/0293701 A1 | 12/2006 | Ainsworth et al. |
| 2007/0010835 A1 | 1/2007 | Breton et al. |
| 2007/0027461 A1 | 2/2007 | Gardiner et al. |
| 2007/0106313 A1 | 5/2007 | Golden et al. |
| 2007/0142848 A1 | 6/2007 | Ainsworth et al. |
| 2007/0150053 A1 | 6/2007 | Gurskis et al. |
| 2008/0119875 A1 | 5/2008 | Ino et al. |
| 2009/0036903 A1 | 2/2009 | Ino et al. |

FOREIGN PATENT DOCUMENTS

| | | |
|---|---|---|
| DE | 0377052 | 6/1923 |
| DE | 2703529 | 1/1977 |
| DE | 3203410 | 5/1981 |
| DE | 3227984 | 2/1984 |
| DE | 3504202 | 8/1985 |
| DE | 4133800 | 10/1991 |
| DE | 4402058 | 4/1995 |
| DE | 19547617 | 9/1997 |
| DE | 197 11 288 | 10/1998 |
| DE | 19732234 | 1/1999 |

| | | |
|---|---|---|
| EP | 0072232 | 2/1983 |
| EP | 0122046 | 3/1983 |
| EP | 0129441 | 12/1984 |
| EP | 0130037 | 1/1985 |
| EP | 0140557 | 5/1985 |
| EP | 0121362 | 9/1987 |
| EP | 0 409 569 | 1/1991 |
| EP | 0409569 | 1/1991 |
| EP | 0432692 | 6/1991 |
| EP | 0478949 | 8/1991 |
| EP | 0494636 | 7/1992 |
| EP | 0537955 | 4/1993 |
| EP | 0559429 | 9/1993 |
| EP | 0598529 | 5/1994 |
| EP | 0326426 | 12/1994 |
| EP | 0419597 | 12/1994 |
| EP | 0632999 | 1/1995 |
| EP | 0641546 | 3/1995 |
| EP | 0656191 | 6/1995 |
| EP | 0687446 | 12/1995 |
| EP | 0705568 | 4/1996 |
| EP | 0711532 | 5/1996 |
| EP | 0705569 | 10/1996 |
| EP | 0734697 | 10/1996 |
| EP | 0778005 | 6/1997 |
| EP | 0815795 | 1/1998 |
| EP | 0 826 340 | 3/1998 |
| FR | 320 731 | 12/1902 |
| GB | 2223410 | 4/1990 |
| JP | 07308322 | 11/1995 |
| JP | 08336544 | 12/1996 |
| JP | 10337291 | 12/1998 |
| RU | 2110222 | 5/1998 |
| SU | 577022 | 10/1977 |
| SU | 1186199 | 10/1985 |
| SU | 1456109 | 2/1989 |
| SU | 1560133 | 4/1990 |
| WO | 90/06725 | 6/1990 |
| WO | 90/09149 | 8/1990 |
| WO | 90/14795 | 12/1990 |
| WO | 91/07916 | 6/1991 |
| WO | 91/08708 | 6/1991 |
| WO | 91/17712 | 11/1991 |
| WO | 92/05828 | 4/1992 |
| WO | 92/12676 | 8/1992 |
| WO | 92/22041 | 12/1992 |
| WO | 93/01750 | 2/1993 |
| WO | 94/15535 | 7/1994 |
| WO | 94/15537 | 7/1994 |
| WO | 96/00035 | 1/1996 |
| WO | 96/06565 | 3/1996 |
| WO | 96/38090 | 12/1996 |
| WO | 97/12555 | 4/1997 |
| WO | 97/16122 | 5/1997 |
| WO | 97/27898 | 8/1997 |
| WO | 97/28744 | 8/1997 |
| WO | 97/31575 | 9/1997 |
| WO | 97/32526 | 9/1997 |
| WO | 97/40754 | 11/1997 |
| WO | 97/42881 | 11/1997 |
| WO | 98/19636 | 5/1998 |
| WO | 98/30153 | 7/1998 |
| WO | 98/42262 | 10/1998 |
| WO | 98/48707 | 11/1998 |
| WO | 98/52475 | 11/1998 |
| WO | 99/07294 | 2/1999 |
| WO | 99/12484 | 3/1999 |
| WO | 99/15088 | 4/1999 |
| WO | 99/37218 | 7/1999 |
| WO | 99/62406 | 12/1999 |
| WO | 99/62408 | 12/1999 |
| WO | 99/62409 | 12/1999 |
| WO | 99/62415 | 12/1999 |
| WO | 99/63910 | 12/1999 |
| WO | 99/65409 | 12/1999 |
| WO | 00/03759 | 1/2000 |
| WO | 00/15144 | 3/2000 |
| WO | 00/44311 | 8/2000 |
| WO | 00/59380 | 10/2000 |
| WO | 00/60995 | 10/2000 |
| WO | 00/64381 | 11/2000 |
| WO | 00/74603 | 12/2000 |
| WO | 01/10310 | 2/2001 |
| WO | 01/19292 | 3/2001 |
| WO | 01/26557 | 4/2001 |
| WO | 01/26586 | 4/2001 |
| WO | 01/28432 | 4/2001 |
| WO | 01/54618 | 8/2001 |
| WO | 01/74254 | 10/2001 |
| WO | 01/82840 | 11/2001 |
| WO | 02/13701 | 2/2002 |
| WO | 02/13702 | 2/2002 |
| WO | 02/30295 | 4/2002 |
| WO | 02/30298 | 4/2002 |
| WO | 02/34143 | 5/2002 |
| WO | 02/080779 | 10/2002 |
| WO | 02/080780 | 10/2002 |
| WO | 02/087425 | 11/2002 |
| WO | 03/053289 | 7/2003 |
| WO | 03/088875 | 10/2003 |
| WO | 2005/011468 | 2/2005 |
| WO | 2005/041784 | 5/2005 |
| WO | 2005/058170 | 6/2005 |
| WO | 2006/060594 | 6/2006 |
| WO | 2007/067942 | 2/2007 |
| WO | 2009/137517 | 11/2009 |

OTHER PUBLICATIONS

US 6,503,260, 01/2003, Schaller et al. (withdrawn).
"VCS Clip Applier System," published in 1995 by Auto Suture Company, a Division of U.S. Surgical Corporation.
Chitwood Jr., Mitral Valve Repair: Ischemic, Mastery of Cardiothoracic Surgery, Lippencott-Raven Publishers, 1998, Chapter 32, pp. 309-321.
Emery, et al., Suture Techniques for MIDCAB Surgery, Techniques for Minimally Invasive Direct Coronary Artery Bypass (MIDCAB) Surgery, R.W. Emery ed., Hanley & Belfus, Inc.: Philadelphia, PA, Chapter 12, 1997, pp. 87-91.
Grondin, et al., Carpentier's Annulus and De Vega's Annuloplasty: The end of the tricuspid challenge, Nov. 1975, vol. 70, pp. 852-861.
Holper, et al., Surgery for Tricuspid Insufficiency: Long Term Follow-Up After De Vega Annuloplasty, Thorac Cardiovasc Surgeon, 41, 1993.
Maisano, et al., The Double Orifice Technique as a Standardized Approach to Treat Mitral Regurgitation Due to Severe Myxomatous Disease: Surgical Technique, European Journal of Cardiothoracic Surgery, vol. 17, 2000, 201-205.
Rabago, et al., The New De Vega Technique In Tricuspid Annuloplasty: Results in 150 patients, J. Cardiovas Surg. 1980, 21 pp. 231-238.
Rivera, et al., Carpentier's Flexible Ring Versus De Vega's Annuloplasty, J Thorac Cardiovas Surg, Feb. 1985, 89 pp. 196-203.
Wei, et al., De Vega's Semicircular Annuloplasty For Tricuspid Valve Regurgitation, Ann Thorac Surg, 1993, 55: pp. 482-485.
Wylie, et al., Manual of Vascular Surgery, R. H. Egdahl ed. Spring-Verlag: New York, vol. II, 1986, Table of Contents only.
Wylie, et al., Manual of Vascular Surgery, Springer-Verlag New York, vol. I, 1980, Table of Contents only.
Yun, et al. Mitral Valve Replacement, Mastery of Cardiothoracic Surgery, Lippencott-Raven Publishers, 1998, Chapter 34, pp. 329-341.
Yun, et al. Mitral Valve Replacement, Mastery of Cardiothoracic Surgery, Lippencott-Raven Publishers, pp. 329-341.
International Search Report PCT/US98/00462.
International Search Report PCT/US98/00795.

International Search Report PCT/US98/14211.
International Search Report PCT/US99/12563.
International Search Report PCT/US99/12566.
International Search Report PCT/US00/09092.
International Search Report PCT/US01/10501.
International Search Report PCT/US01/31709.
International Search Report PCT/US01/42653.
International Search Report PCT/US02/10865.
International Search Report PCT/US02/10866.
International Search Report PCT/US02/14261.
International Search Report PCT/US03/12073.
International Preliminary Examination Report PCT/US98/00462.
International Preliminary Examination Report PCT/US98/00795.
International Preliminary Examination Report PCT/US99/12566.
International Preliminary Examination Report PCT/US00/09092.
International Preliminary Examination Report PCT/US01/31709.
International Preliminary Examination Report PCT/US01/42653.
International Preliminary Examination Report PCT/US02/14261.
International Preliminary Examination Report PCT/US02/10865.
International Preliminary Examination Report PCT/US02/10866.
International Preliminary Examination Report PCT/US03/12073.
Written Opinion PCT/US99/12563.
Written Opinion PCT/US99/12566.
Written Opinion PCT/US00/09092.
Written Opinion PCT/US01/10501.
Written Opinion PCT/US01/31709.
Written Opinion PCT/US02/10866.
Written Opinion PCT/US02/14261.
Written Opinion PCT/US03/12073.
International Preliminary Report on Patentability PCT/US2004/023728.

* cited by examiner

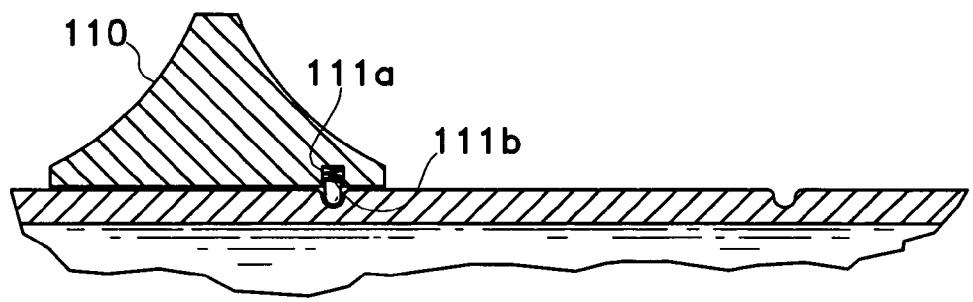
Fig. 1C
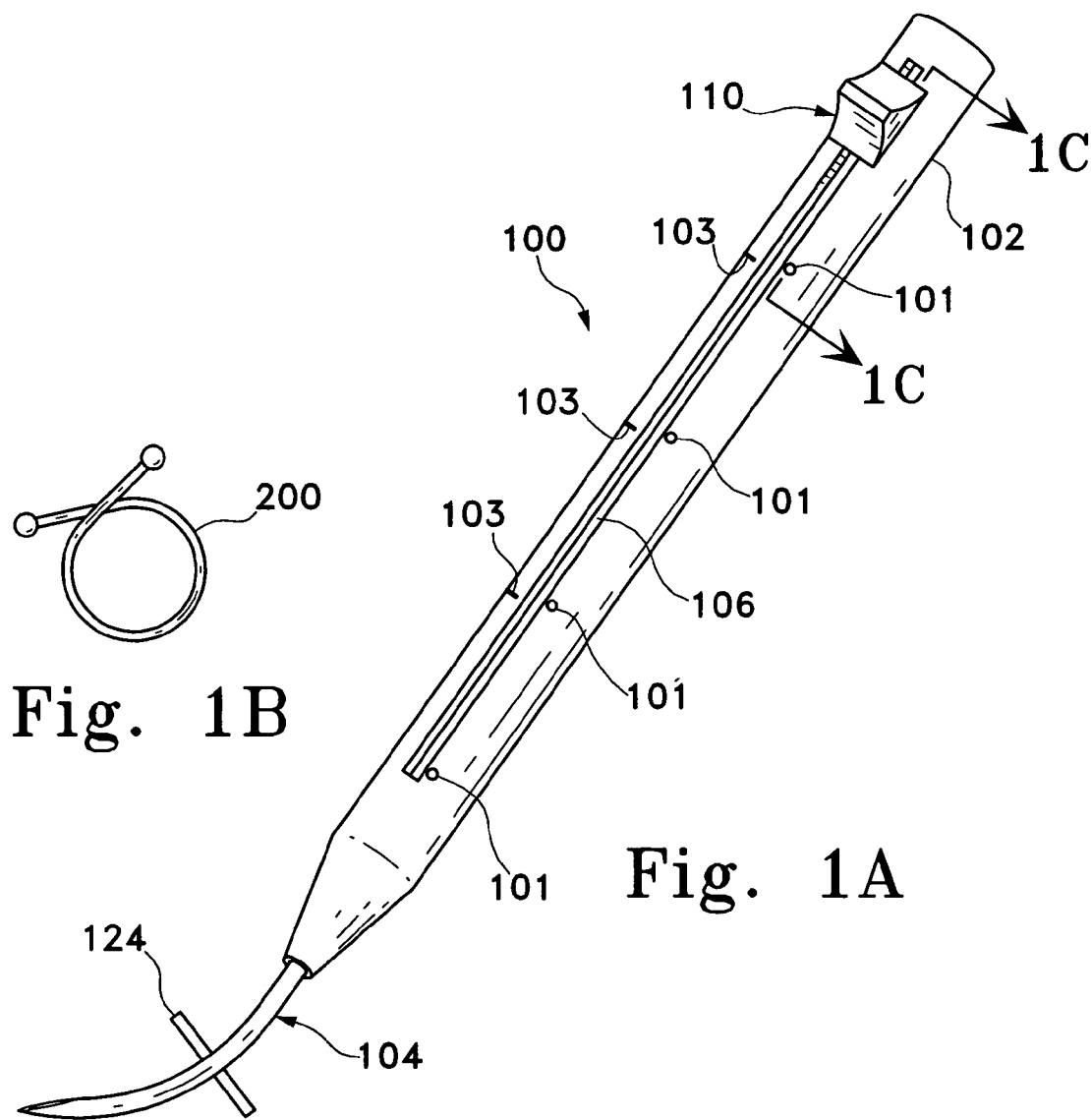
Fig. 1B
Fig. 1A

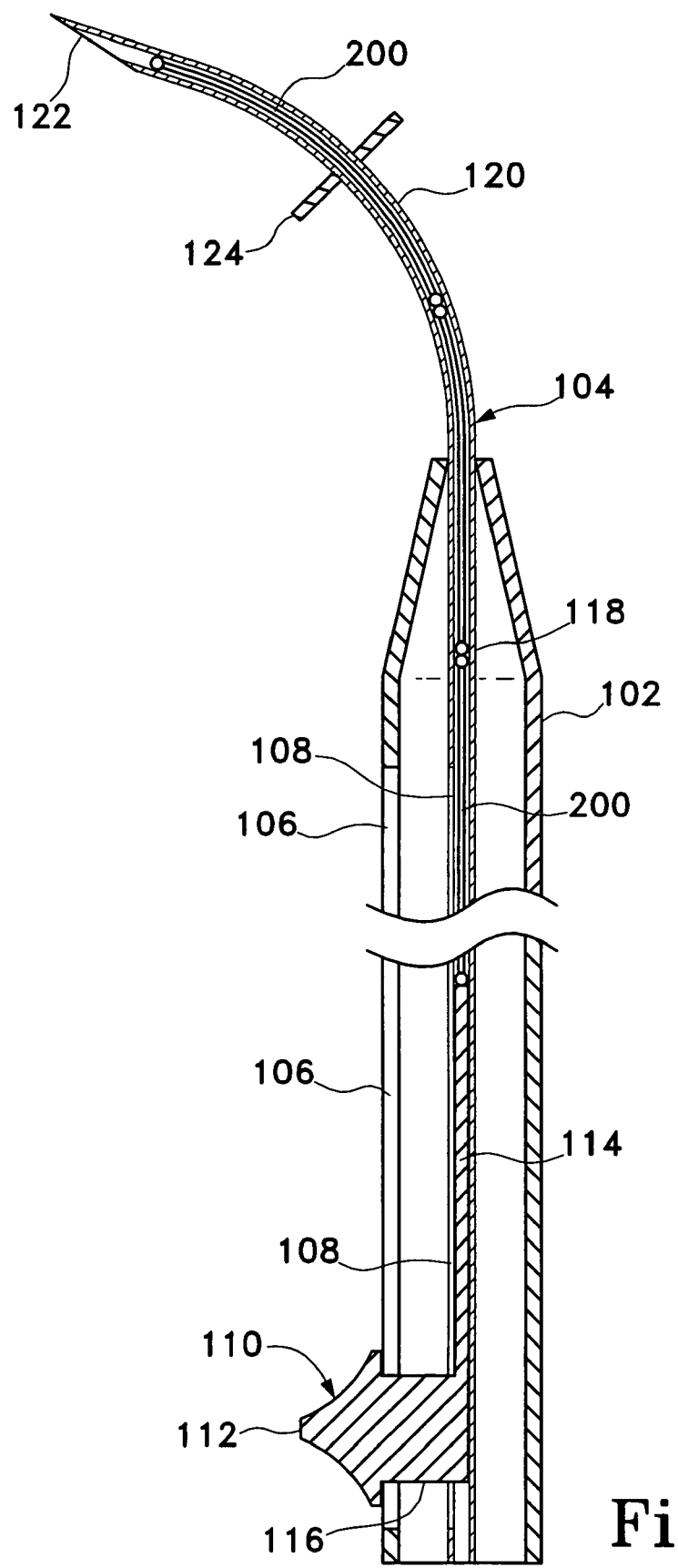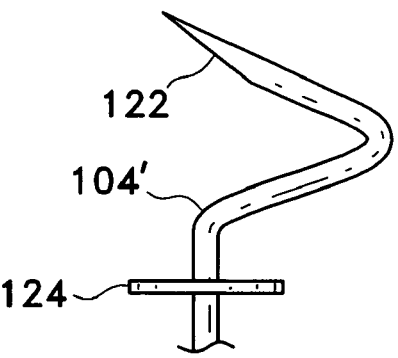
Fig. 2B
Fig. 2A

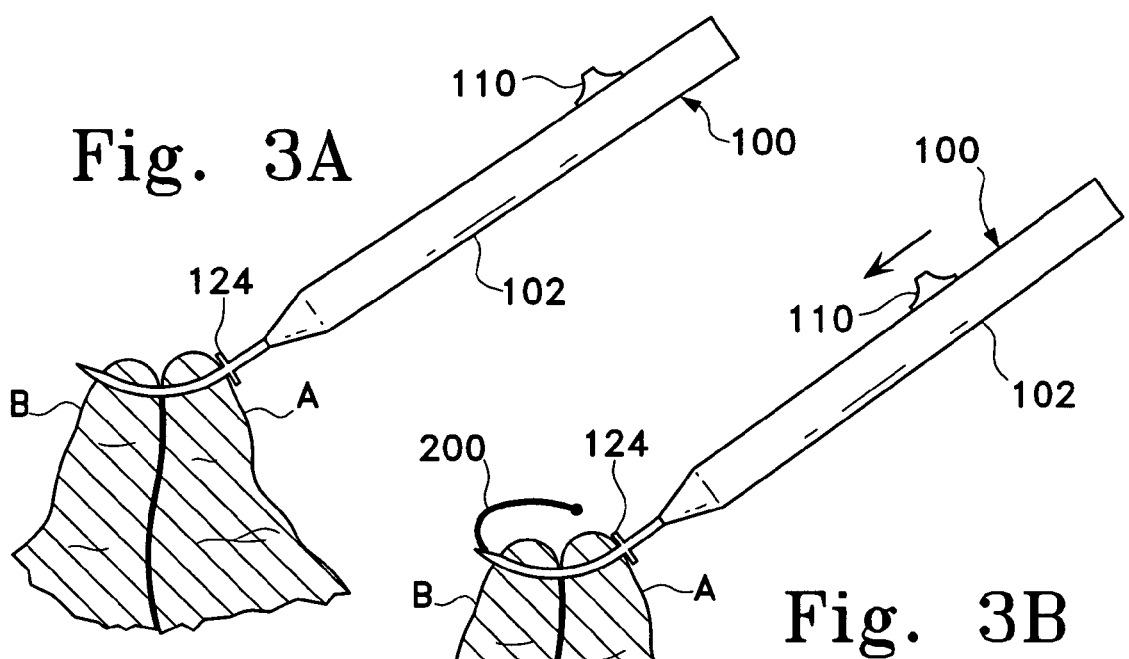
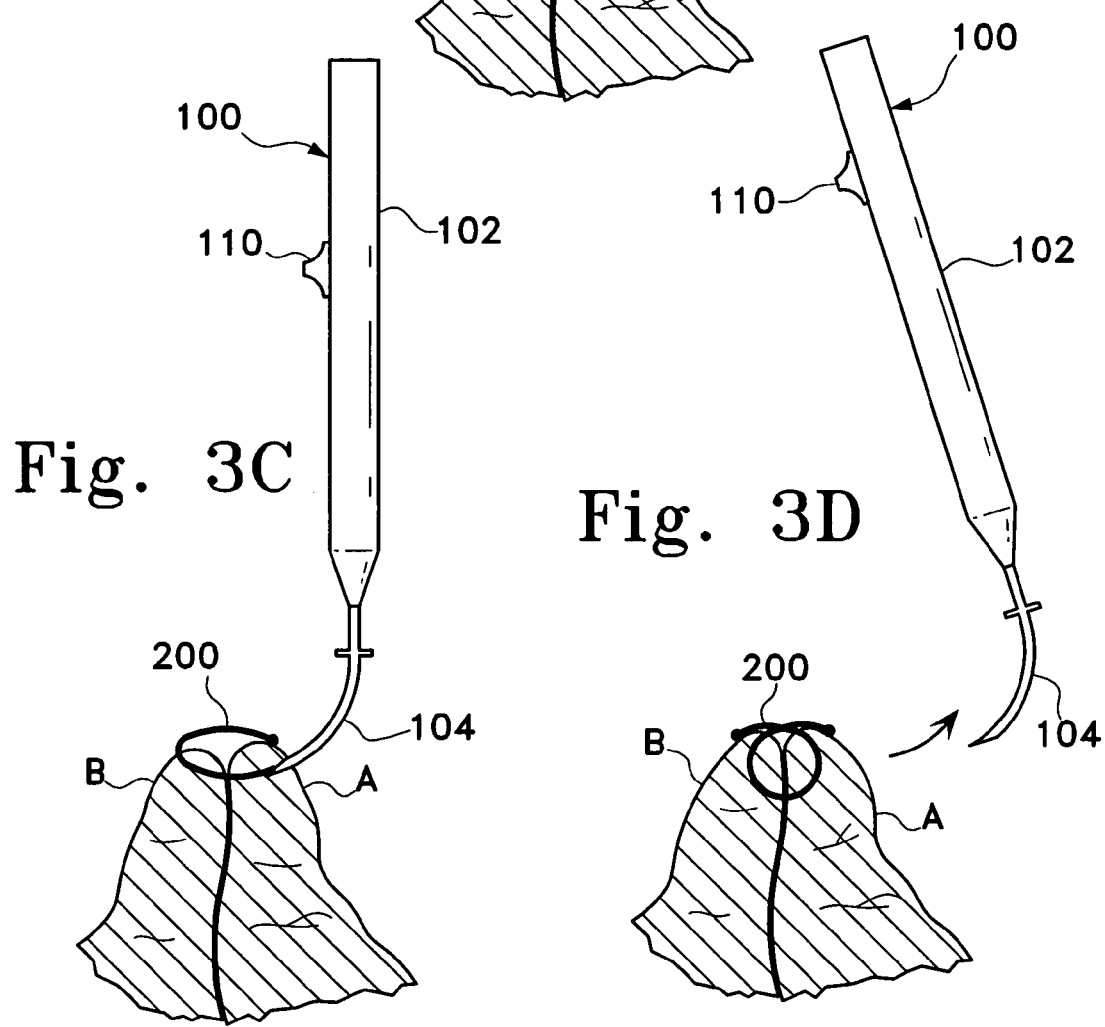

SURGICAL CONNECTION APPARATUS AND METHODS

FIELD OF THE INVENTION

This invention relates to apparatus and methods for joining structures in surgical procedures such as in laparoscopic procedures.

BACKGROUND OF THE INVENTION

Suturing tissue laparoscopically has always been challenging. Over the past fifteen years or so, there have been many devices developed and marketed to solve this problem. Linear staplers have been the most successful of these devices, but they have limitations. One of the limitations of stapling devices is that one can only place the staples in a pre-determined, confined, straight row. Other stitching type or needle-passing type devices also have been marketed with limited acceptance. Needle management is one concern with these devices. Needle manipulation and knot tying difficulties in confined spaces also have presented concerns. Surgical fasteners or clips, which address suture knot tying problems, are disclosed, for example, in U.S. Pat. No. 6,607,541 to Gardiner, et al., U.S. Pat. No. 6,514,265 to Ho, et al., U.S. Pat. No. 6,613,059 to Schaller, et al. and U.S. Pat. No. 6,641,593 to Schaller, et al. There remains a need to improve apparatus and methods for joining structures in surgical procedures.

SUMMARY OF THE INVENTION

The present invention involves improvements in surgical connection apparatus and methods. Among the many advantages of the invention is it can be used to readily deliver surgical clips to a surgical site to connect tissue and can eliminate or minimize the need for suturing.

According to one embodiment of the invention, surgical connection apparatus comprises a tubular needle having a proximal portion and a distal portion with a pointed distal end, the tubular needle forming a pathway between the proximal and distal portions; a plurality of self-closing clips, each clip being slidably disposed in the pathway; and a pusher having at least a portion arranged to slidably move in the pathway and push the clips in a distal direction.

According to another embodiment of the invention, surgical connection apparatus comprises a support having a distal portion having a distal end and a proximal portion, the support forming a pathway between the proximal and distal portions; a plurality of self-closing clips, each clip being slidably disposed in the pathway; a pusher having at least a portion arranged to slidably move in the pathway and push the clips in a distal direction; and a stop member extending from said distal portion of the support at a location spaced from the distal end of the support and along the pathway a distance sufficient to allow gathering on the distal portion of the support material to be joined.

According to another embodiment of the invention, surgical connection apparatus comprises a support having a distal portion having a distal end and a proximal portion, the support forming a pathway between the proximal and distal portions; a plurality of self-closing clips, each clip being slidably disposed in the pathway; a pusher having at least a portion arranged to slidably move in the pathway and push the clips in a distal direction; and a stop member extending from the distal portion of the support at a location measured from the distal end of the support and along the pathway a distance less than the length of one of the self-closing clips.

According to another embodiment of the invention, surgical connection apparatus comprises a support having a distal portion having a distal end and a proximal portion, the support forming a pathway between the proximal and distal portions; a plurality of self-closing clips, each clip being slidably disposed in the pathway; and a pusher having at least a portion arranged to slidably move in the pathway and push the clips in a distal direction, the pusher having a first state where it is releasably locked in a first position in the support with one of the clips being in the distal portion of the support and a second state where it is releasably locked in a second position in the support with the one of the clips being partially ejected from the support.

According to another embodiment of the invention, surgical connection apparatus comprising a tubular clip support having a distal portion having a distal end and a proximal portion, the support forming a pathway between the proximal and distal portions, the support having a slot formed therein; a plurality of self-closing clips, each clip being slidably disposed in the pathway; a tubular sleeve surrounding at least a portion of the tubular clip support and having a slot aligned with the slot in the tubular clip support; and a pusher having at least a portion arranged to slidably move in the pathway and push the clips in a distal direction, the pusher extending through the slots.

According to another embodiment, a method of connecting tissue comprises penetrating a self-closing clip support through first and second portions of material wherein at least one of the portions comprises tissue; extending a portion of a self-closing clip from the clip support; and simultaneously withdrawing the clip support from said material and allowing the self-closing clip to be discharged therefrom.

According to another embodiment, a method of connecting tissue comprises penetrating a self-closing clip support through first and second portions of material wherein at least one of the portions comprises tissue; extending a portion of a self-closing clip, having a memory set closed configuration, from the clip support and allowing the extended portion to move toward its memory set closed configuration; withdrawing the clip support from the material and allowing the self-closing clip to be completely withdrawn from the support and move toward its closed configuration.

The above is a brief description of some deficiencies in the prior art and advantages of the present invention. Other features, advantages, and embodiments of the invention will be apparent to those skilled in the art from the following description, accompanying drawings, wherein, for purposes of illustration only, specific forms of the invention are set forth in detail.

BRIEF DESCRIPTION OF THE DRAWINGS

FIG. 1A is a perspective view of a tissue connecting device in accordance with the present invention;

FIG. 1B illustrates a surgical clip released from the device of FIG. 1A;

FIG. 1C is a sectional view taken along line 1C-1C in FIG. 1A;

FIG. 2A is a longitudinal sectional view of the device of FIG. 1A;

FIG. 2B depicts a variation of the device illustrated in FIG. 2A;

FIGS. 3A-D illustrate an exemplary use of the device of FIG. 1A where FIG. 3A shows the device positioned in tissue, FIG. 3B depicts partial ejection of a clip from the device of FIG. 3A, FIG. 3C illustrates withdrawal of the device and withdrawal of the clip therefrom, and FIG. 3D illustrates the clip fully released and in a closed configuration.

DETAILED DESCRIPTION OF THE INVENTION

Before the present invention is described, it is to be understood that this invention is not intended to be limited to particular embodiments or examples described, as such may, of course, vary. Further, when referring to the drawings, like numerals indicate like elements.

The devices, apparatus, and methods described herein generally can be used to surgically connect structures in a patient. They can be used to connect tissue, tissue and prosthetic material, or tissue and graft material. They can be used in endoscopic procedures such as laparoscopic procedures involving connection of tissue within the peritoneal cavity. One example of such procedures is a gastrointestinal bypass procedure. They can be used to connect nontubular or tubular structures. For example, the devices and apparatus described herein can be used to anastomose tubular structures or conduits. The tubular structures can be vascular or nonvascular structures, which can include, but are not limited to, the bile duct, urethra, urinary bladder, intestines, esophagus, stomach, and bowel.

In various embodiments described herein, surgical clips are delivered with a clip support or carrier, which among other things can be used to facilitate approximation of the tissue or material to be joined in addition to carrying the clips.

Referring to FIGS. 1A and B, one embodiment of surgical connection apparatus in accordance with the principles of the present invention is illustrated and generally designated with reference numeral 100. Surgical connection apparatus or device 100 generally includes outer housing or support 102 and clip support or carrier 104. Clip support 104 forms a pathway for a plurality of clips, e.g., clips 200, to be partially ejected and then withdrawn therefrom. Outer housing or support 102 and clip support 104 can be in the form of tubular members and clip support 104 can be a hypo-needle. Among the many advantages of clip support 104 is it can be sized and/or configured for insertion through endoscopic access ports. Clip support 104 also can be advantageously sized and/or configured to penetrate the tissue or material to be joined. One of the many advantages of this configuration is that the clip support can be used to penetrate the tissue or material to be joined instead of using the clip carried thereby, which can eliminate the need for introducing a clip with a sharp end and leaving such a clip at the surgical site.

An actuator or pusher for discharging clips is provided. One example of an actuator or pusher according to the present invention is illustrated in FIGS. 1A and 2A and is generally designated with reference numeral 110. Referring to FIGS. 1A and 2A, actuator 110 moves along slots 106 and 108. Slot 106 is formed in outer housing 102 and extends in a longitudinal direction between the proximal and distal ends thereof. Slot 108 (FIG. 2A) is formed in support 104, extends between the proximal and distal ends thereof, and is aligned with slot 106. Actuator or ejector 110 forms a clip pusher and includes first portion 112, second portion 114, and connecting portion 116. First portion 112 slides or tracks along slot 106 and can be in the form of a button. Second portion 114 tracks inside clip support 104 and forms a pusher rod or member for pushing clips 200 out from apparatus 100. That is, second portion 114 is slidably disposed in the pathway or lumen defined by clip support 104. Second portion 114 can be an elongated member and can be flexible so that it can readily move inside the curved distal end portion 120 of clip support 104. Connecting portion 116 interconnects portions 112 and 114.

Although one actuator or ejector configuration is shown, other configurations can be used. According to one variation, the actuator can comprise a pusher rod disposed in the clip support pathway or lumen with its distal end arranged to push clips distally and its proximal end extending proximally and axially from the proximal end of clip support 104 and housing 102.

Clip support 104 can be shaped so that it can be inserted into the material or tissue with a single motion of the wrist and then withdrawn with a single motion of the wrist. In the illustrative embodiment, clip support 104 has a straight portion 118, shown inside housing 102 in FIG. 2A, and a curved distal end portion 120. The curved portion can improve or simplify manipulation of the distal end portion through materials to be joined as described above and shown in FIGS. 3A-D. Clip support 104 or distal end portion 120 also can have a beveled or sharpened end portion 122 which presents a surface that faces inwardly and which forms a pointed tip as shown in FIG. 2A. This can enhance the ability of the clip support to penetrate tissue or material to be joined.

Apparatus 100 can be provided with a mechanism to indicate clip position. This mechanism can be used to control the degree or extent of ejection of a respective clip. According to one embodiment, a stopper 124, which can be in the form of a disk, for example, can be secured to the distal portion of clip support 104 to control the degree of penetration of clip support 104. In the illustrative embodiment, the stopper extends from the distal portion of the clip support at a location spaced from the distal end of the clip support and along the clip pathway a distance less than the length of one of the self-closing clips. Preferably this distance will be about one-half the length of one clip and thus ranges from about ⅛ to about 1 inch depending on the application. For example, in laparoscopic procedures for connecting bowel tissue to bowel tissue, this distance will be about ¼ inch (the clip length being about ½ inch). The following is provided to illustrate how the stopper position can facilitate partial clip ejection control or calibration. Specifically, after at least a portion of the clip support forward of the stopper is positioned in the material to be joined, actuator 110 can be moved to partially eject a clip to a position where its distal end is adjacent to the stopper (FIG. 3B). The ejected portion of the clip, which in the illustrative embodiment is about one-half of the clip, moves toward a closed position and forms a hook to grip the material to be joined. With the distal end of the clip adjacent to the stopper, the remaining portion of the clip, which in the illustrative example, is about half of the clip, is then withdrawn from device 100 as device 100 is removed from the attachment site. Accordingly, one of the many advantages of the stopper arrangement is that the relative position of the ejected distal end of a clip and the stopper can be used to indicate the extent of clip ejection and/or to control clip position.

According to a further embodiment, apparatus 100 can be provided with an alternative or additional mechanism to indicate clip position. This mechanism indicates the position of actuator 110 to facilitate control of the degree or extent of ejection of a respective clip. The pusher can have a first state where it is releasably locked in a first position in support 104 with the distal most clip being within the support and a second state where it is releasably locked in a second position in support 104 with the distal most clip being partially ejected from the support. One example of such a mechanism is shown is shown in FIGS. 1A and C.

Referring to FIGS. 1A and C, the alternative or additional mechanism for indicating clip position comprises a plurality of recesses or depressions 101 formed in outer housing 102, a bore 111a formed in the actuator first portion 112 and a button and spring combination 111b, which is seated in bore 111a. The button can have a spherical shape or other suitable shape as is known in the art. The spring urges the button or post to lockingly engage a respective recess 101, but permits disengagement when sufficient force is applied to actuator 110. Recesses are positioned to facilitate the desired degree of ejection of each clip. For example, if in the initially fully loaded state, the distal most clip is positioned at the distal end of clip support 104 and about one-half of a respective clip 200 is to be ejected, the proximal most recess 101 and recess 101 adjacent thereto can be spaced apart a distance corresponding to about one-half the length of a clip 200 so that movement of actuator 110 from the proximal most recess 101 to the next extends about one-half of the distal most clip out from clip support 104. Since the partially extended clip is then withdrawn from apparatus 100 as described in more detail below, the next clip up for partial ejection will remain spaced from the distal end of clip support 104 by about one-half the length of a clip. Its distal end will be close to where the proximal end of the first partially ejected clip was before the first partially ejected clip was withdrawn and fully removed from apparatus 100. Accordingly, the remaining distance between recesses 101 can correspond to the full length of a clip so that movement of the actuator from one recess 101 to the next recess 101 partially ejects a clip with about one-half the length of the clip extending from clip support 104 and being exposed.

Although one detent mechanism has been described for purposes of illustration, other detent configurations can be used as well as other ejection indicators or control mechanisms. For example, a spring loaded button can be seated in each of the recesses 101 and bore 111a left empty for engagement therewith. According to a further example, indicia can be provided to indicate a predetermined degree of clip ejection when actuator 110 is aligned therewith. Referring to FIG. 2A, exemplary indicia are shown and indicated with reference numeral 103. The outer distal edge of actuator 110 can be aligned with a respective marking 103 to indicate the degree of clip ejection. The clip position indicators described above can be used alone or in any combination thereof. For example, stopper 124 can be used in combination with the illustrative detent arrangement as shown in FIGS. 1A and C.

Further, although clip support 104 is shown with one configuration, others can be used. For example, the distal end portion of clip support 104 can be provided with a corkscrew shape with either a straight or curved center axis. The corkscrew portion can have a one-half or three-quarter turn, for example. When a corkscrew shape and straight center axis is used as shown in FIG. 2B, one can simply rotate outer housing or shaft 102 so that the clip is withdrawn from clip support 104 as the corkscrew shaped distal portion is withdrawn from the materials being joined. Referring to FIG. 2B, the corkscrew variation of the clip support is designated with reference numeral 104'. Other than the corkscrew configuration at the distal portion of clip support 104' and the hypo-needle straight portion extending a small distance beyond stopper 124, clip support 104' as shown in FIG. 2B is the same as clip support 104.

As described above, clips 200 can be disposed inside clip support 104 as shown in FIG. 2A. The clips are aligned serially and, thus, can be ejected or applied consecutively without the need to withdraw the device or clip support 104 from the endoscopic or access port to reload. The number of clips which can be housed in clip support 104 is a function of clip size and the length of the clip support. Clip support or hypo-needle 104 constrains the clips in an open position and provides a means of tissue penetration. In operation, clip support 104 is penetrated through the target material. It can have a pointed or sharpened distal end as described above to enhance its ability to readily penetrate tissue or material to be joined. As will described in more detail below, each clip is partially ejected from the device via actuator 110 after which device 100 is withdrawn, thus allowing closure of the clip. Using the clip support to penetrate tissue can eliminate the need to penetrate tissue with the clip and the need to use a clip having one or more sharp ends. Accordingly, clips 200 can have two non-pointed or rounded ends. Although ball shaped or spherically shaped ends are shown in the illustrative embodiment, other shapes providing non-pointed ends can be used as well.

Returning to FIG. 1B, one suitable clip configuration is shown. In the illustrative embodiment, surgical clip 200 includes ball shaped proximal and distal ends and a loop shaped memory set shape or configuration. Although clip 200 is shown with an overlapping loop closed configuration, it can be non-overlapping or otherwise shaped differently than that shown when in its memory set closed shape.

Clips 200 are self-closing clips in that they return toward their memory set configuration after being released from a deformed configuration.

Self-closing clips 200 can be made from nitinol wire and provided with the desired memory set configuration to exhibit pseudoelastic (supereastic) behavior. In other words, at least a portion of the shape memory alloy is converted from its austenitic phase to its martensitic phase when the wire is in its deformed configuration. As the stress is removed, the material undergoes a martensitic to austenitic conversion and springs back to its original undeformed configuration.

The shape memory alloy can be selected with a transformation temperature suitable for use with a stopped heart condition where cold cardioplegia has been injected for temporary paralysis of the heart tissue (e.g., temperatures as low as 8-10 degrees Celsius).

The cross-sectional diameter of the wire and length of the wire will vary depending on the specific application. The diameter of the wire may be, for example, between 0.004 and 0.025 inch and the diameter of the wire loop may range from about 0.020 to about 0.500 inch. The wire may be formed in a loop shape by first wrapping the wire onto a mandrel and heat treating the wire at approximately 400-500 degrees Celsius for approximately 5 to 30 minutes. The wire is then air quenched at room temperature.

It is to be understood that the shape memory alloy may also be heat activated, or a combination of heat activation and pseudoelastic properties may be used as is well known by those skilled in the art.

Clip support 104 can be formed from a hypo-needle, which can be made from a piece of surgical grade stainless steel tubing, one end of which can be beveled and sharpened. Beveled and sharpened hypo-needles are common in the industry. One end portion of the hypo-needle can be shaped to have a curvature as described above. The outer housing 102 forms a shaft or handle for clip support 104 and can be machined metal, injection-molded plastic, or extruded plastic. Housing 102 also can be formed as a single unitary structure or a combination of joined parts.

The following describes an exemplary use of apparatus 100 and is not intended to limit the invention. This example is illustrative of connecting tissue to tissue within the peritoneal cavity. It should be understood that the device can be used to connect other tissue or materials as described above.

In accordance with the example, a distal end portion of clip support 104 of apparatus 100 is inserted through a laparascopic port where the distal end of clip support or hypo-needle 104 is manipulated to penetrate or pierce a first portion "A" of target tissue and then to penetrate or pierce another portion "B" of the same or different target tissue, which prior to the procedure may be spaced from one another. Penetration through portions A and B can be accomplished with a single twist or motion of the wrist. Observation can be accomplished through placement of an endoscopic camera in another port as is known in the art. The clip support or hypo-needle 104 is positioned so that it completely penetrates through both portions of tissue and the stopper is in contact with the first portion as shown in FIG. 3A. In this position only the sharp tip of the hypo-needle should be visibly protruding from the second portion of tissue of tissue (FIG. 3A). Clip support 104 can effect or facilitate tissue approximation as it is passed through both tissue portions and manipulated. Stopper 124 also can be positioned to facilitate tissue manipulation and/or approximation as it can be used to push one tissue portion against the other. Accordingly, stopper 124 can be positioned so that it extends from the distal portion of clip support 104 at a location spaced from the distal end of clip support 124 and along the clip pathway defined by the support (e.g., the clip support lumen when a tubular support is used) a distance sufficient to allow gathering on the clip support material to be joined. The distance typically will range from about ⅛ inch to about 1 inch depending on the application.

Referring to FIG. 3B, actuator 110 is moved distally or forward so that a distal end portion of the distal most clip in the hypo-needle is extended therefrom and its distal end just covers the seam between the two portions of tissue (FIG. 3B). In this example, the distal end of the clip is adjacent to stopper 124 indicating that about one-half the clip has been ejected. Apparatus 100 can alternatively or in addition include a further mechanism to indicate the position of a respective clip (e.g., partial ejection such as ejection of one-half of the clip) as described above in connection with FIGS. 1A and C.

The hypo-needle is then withdrawn from the tissue in the opposite direction from its entry as shown in FIG. 3C. The surgeon can accomplish this with a slight twist or single motion of the wrist or a slight reverse-pull motion. As the hypo-needle is withdrawn, the proximal portion of the clip, which was held inside the hypo-needle by friction, is withdrawn and remains in the tissue. After the clip is fully withdrawn from the hypo-needle, it moves toward its shape memory set closed configuration (FIG. 3D) and holds the tissue together. Clip support 104 of apparatus 100, which was loaded with a plurality of clips 200, can then be manipulated to reposition the clip support along the tissue portions or seam to deploy another clip. This can be done without removing the distal end of clip support 104 from the endoscopic port. After the procedure is completed, the clip support or hypo-needle is retracted. The foregoing procedure involves or uses a single needle, hypo-needle 104, and thus can eliminate or minimize needle management concerns.

Any feature or combination of features of any one embodiment described herein can be combined with any other feature or combination of features of one or more of the other embodiments.

Variations and modifications of the devices and methods disclosed herein will be readily apparent to persons skilled in the art. As such, it should be understood that the foregoing detailed description and the accompanying illustrations, are made for purposes of clarity and understanding, and are not intended to limit the scope of the invention, which is defined by the claims appended hereto.

What is claimed is:

1. Surgical connection apparatus comprising:
a tubular needle having a proximal portion and a distal portion with a pointed distal end, said tubular needle forming an interior pathway at least a portion of which being within said tubular needle between said proximal and distal portions;
a plurality of self-closing clips, each clip being slidably disposed in said pathway; and
a pusher having a portion arranged to slidably move in said at least a portion of said pathway and push and move said clips in a distal direction, including said pusher arranged to fully deploy a distal-most one of said clips from said distal end without movement of said needle relative to said pusher
wherein each clip has a first end and a second end, and both of said ends are ball shaped.

2. Surgical connection apparatus comprising:
a support having a distal portion having a distal end and a proximal portion, said support forming an interior pathway between said proximal and distal portions, said pathway being circumferentially closed along said distal portion and open at said distal end;
a plurality of self-closing clips, each clip being slidably disposed in said pathway;
a pusher having a portion arranged to slidably move in said pathway and push said clips in a distal direction; and
a stop member in contact with and extending from said distal portion of said support;
wherein said support comprises a tubular member, which forms at least a portion of said pathway, each clip has a memory set closed configuration, when said clips are disposed in said tubular member, said tubular member biases said clips away from said closed configuration, and when said clips are released from said tubular member, said clips move toward their memory set closed configuration, wherein each clip has a ball shaped first end and a ball shaped second end.

3. The apparatus of claim 2 wherein said support comprises a tubular member and said self-closing clips are slidably disposed in said tubular member and serially arranged.

4. The apparatus of claim 2 wherein said support distal portion is curved.

5. The apparatus of claim 2 wherein said support distal portion has a spiral portion.

6. The apparatus of claim 2 wherein said support member comprises a tubular member and said distal end is pointed.

7. The apparatus of claim 6 wherein said tubular member comprises a hypo-needle.

8. The apparatus of claim 7 wherein said hypo-needle has a slot formed therein, said slot extending toward said distal end of said support and said pusher having a portion extending through said slot.

9. The apparatus of claim 2 wherein said clips have a loop shaped memory set closed configuration.

10. The apparatus of claim 9 wherein said support comprises a tubular member and said self-closing clips are slidably disposed in said tubular member and serially arranged.

11. The apparatus of claim 2 wherein said distance ranges from about ⅛ inch to about 1 inch.

12. The apparatus of claim 2 wherein support comprises a tubular needle and said stop member extends radially from said needle.

13. The apparatus of claim 12 wherein said stop member is secured to said tubular needle.

14. The apparatus of claim 13 wherein said stop member is disk shaped.

15. The apparatus of claim 2 wherein said support comprises a tubular needle, at least a portion of said pathway is within said tubular needle, and said pusher has a portion arranged to slidably move in said at least a portion of said pathway and push said clips in a distal direction.

16. The apparatus of claim 2 wherein each clip is a discrete, separate element.

17. Surgical connection apparatus comprising:
 a support having a distal portion having a distal end and a proximal portion, said support forming a pathway between said proximal and distal portions;
 a plurality of self-closing clips, each clip being slidably disposed in said pathway; and
 a pusher having a portion arranged to slidably move in said pathway and push said clips in a distal direction, said pusher having a first state where it is releasably locked in a first position in said support with one of said clips being in the distal portion of said support and a second state where it is releasably locked in a second position in said support with said one of said clips being partially ejected from said support;
 wherein said support comprises a tubular member and said distal end is pointed;
 wherein said tubular member comprises a hypo-needle;
 wherein said hypo-needle has a slot formed therein, said slot extending toward said distal end of said support and said pusher extending through said slot; and
 including a second tubular member surrounding a portion of said support and having a slot formed therein and aligned with said slot in said hypo-needle, said pusher extending through both slots;
 wherein said second tubular member has a plurality of recesses and said pusher has a recess, further including a spring loaded button disposed in said pusher recess and said pusher being movable to align said spring loaded button with said second tubular member recesses.

18. Surgical connection apparatus comprising:
 a tubular clip support having a distal portion having a distal end and a proximal portion, said support forming a pathway between said proximal and distal portions, said support having a slot formed therein;
 a plurality of self-closing clips, each clip being slidably disposed in said pathway;
 a tubular sleeve surrounding at least a portion of said tubular clip support and having a slot aligned with said slot in said tubular clip support; and
 a pusher arranged to slidably move in said pathway and push said clips in a distal direction, said pusher extending through said slots;
 wherein said pusher has a first state where it is releasably locked in a first position in said support with one of said clips being within the distal portion of said support and a second state where it is releasably locked in a second position in said support with said one of said clips being partially ejected from said support;
 wherein said tubular sleeve has a plurality of recesses and said pusher has a recess, further including a spring loaded button being disposed in said pusher recess and said pusher being movable to align said spring loaded button with said tubular sleeve recesses.

* * * * *